(12) United States Patent
Pacey (10) Patent No.: US 11,135,048 B2
(45) Date of Patent: Oct. 5, 2021

(54) DISTRIBUTED PRESSURE FENESTRATED URETHRAL COMPRESSION APPARATUS FOR TREATMENT OF MALE URINARY SPHINCTER DEFICIENCY WITH PRESERVATION OF BLOOD FLOW

(71) Applicant: Pacey Medtech Ltd., Vancouver (CA)

(72) Inventor: John Allen Pacey, Vancouver (CA)

(73) Assignee: Pacey Medtech Ltd., Vancouver BC (CA)

( * ) Notice: Subject to any disclaimer, the term of this patent is extended or adjusted under 35 U.S.C. 154(b) by 95 days.

(21) Appl. No.: 16/473,277

(22) PCT Filed: Jun. 16, 2017

(86) PCT No.: PCT/CA2017/050737
§ 371 (c)(1),
(2) Date: Jun. 25, 2019

(87) PCT Pub. No.: WO2018/137020
PCT Pub. Date: Aug. 2, 2018

(65) Prior Publication Data
US 2019/0314129 A1    Oct. 17, 2019

Related U.S. Application Data

(60) Provisional application No. 62/480,472, filed on Apr. 2, 2017, provisional application No. 62/450,144, filed on Jan. 25, 2017.

(51) Int. Cl.
*A61F 2/00* (2006.01)
*A61B 5/00* (2006.01)
(Continued)

(52) U.S. Cl.
CPC .......... *A61F 2/0054* (2013.01); *A61B 5/0008* (2013.01); *A61B 5/14551* (2013.01);
(Continued)

(58) Field of Classification Search
CPC ........ A61F 2/00; A61F 2/0004; A61F 2/0031; A61F 2/0054; A61F 2230/0002–0006;
(Continued)

(56) References Cited

U.S. PATENT DOCUMENTS

| 678,943 A | * | 7/1901 | Davis | A61F 5/0096 128/883 |
| 1,728,322 A | | 9/1929 | Badrian | |

(Continued)

FOREIGN PATENT DOCUMENTS

| IT | MI20082328 A1 | 6/2010 |
| WO | WO2007130977 A1 | 11/2007 |

OTHER PUBLICATIONS

Written Opinion of the International Search Authority and International Search Report, PCT/CA2017/050737; dated Oct. 2, 2017.
(Continued)

*Primary Examiner* — Michelle J Lee
(74) *Attorney, Agent, or Firm* — Hancock Hughey LLP (57) ABSTRACT

An urethral compression apparatus is defined by a semi-cylindrical fenestrated dorsal hood that is worn dorsally on the penis and which is interconnected with a strap to a urethral compressor that is oriented ventrally to apply compressive pressure on the urethra to prevent urine leakage. The dorsal hood and the urethral compressor apply distributed pressure that prevents compromised venous and arterial circulation but eliminate incontinence. The device may be worn continually and is easily removed to allow voiding, then reattached. The fenestration in the dorsal hood (or plural fenestrations as the case may be) allows distribution of pressure to avoid venous and arterial blood flow interruption. The dorsal hood partially encircles the penile shaft and the urethral compressor is oriented ventrally and applies the desired pressure to the soft ventral tissues and the urethra. A strap applies tension between the dorsal hood and
(Continued)

the urethral compressor, and thus the necessary compression between these two components.

18 Claims, 7 Drawing Sheets

(51) Int. Cl.
*A61B 5/1455* (2006.01)
*A61B 5/20* (2006.01)

(52) U.S. Cl.
CPC .......... *A61B 5/4836* (2013.01); *A61B 5/6813* (2013.01); *A61B 5/6831* (2013.01); *A61F 2230/0013* (2013.01); *A61F 2250/001* (2013.01); *A61F 2250/0097* (2013.01)

(58) Field of Classification Search
CPC ................ A61F 5/41; A61F 2005/411; A61F 2005/414; A61F 2005/415; A61F 2230/0013; A61F 5/0096; A61F 5/0041; A61F 6/20–208; A61F 2250/0004; A61F 2250/001; A61F 2250/0096; A61F 2250/0097; A61F 2250/00–0002; A61B 17/132–1327; A61B 17/12–12013; A61B 17/122–1327; A61B 5/00; A61B 5/0002; A61B 5/0004; A61B 5/0008; A61B 5/145; A61B 5/1455; A61B 5/14551; A61B 5/20; A61B 5/48; A61B 5/4836; A61B 5/68–6802; A61B 5/6801; A61B 5/6813; A61B 5/683; A61B 5/6831
See application file for complete search history.

(56) References Cited

U.S. PATENT DOCUMENTS

| | | | | |
|---|---|---|---|---|
| 2,754,825 A * | 7/1956 | Richmond | ......... | A61B 17/1327 606/203 |
| 3,155,096 A * | 11/1964 | Outwin | ................ | A61B 17/122 128/885 |
| 3,570,496 A * | 3/1971 | Sachs | ................. | A61B 17/1325 606/203 |
| 3,636,948 A * | 1/1972 | Atchley | .................... | A61F 5/41 600/41 |
| 4,880,016 A | 11/1989 | Worth et al. | | |
| 4,942,886 A | 7/1990 | Timmons | | |
| 5,184,629 A | 2/1993 | Erickson | | |
| 5,571,125 A | 11/1996 | Chadwick | | |
| 5,842,968 A * | 12/1998 | Johnson | ................ | A61F 2/0054 600/38 |
| 5,860,911 A * | 1/1999 | Dolade Guardia | ... | A61F 2/0054 600/39 |
| 6,349,727 B1 | 2/2002 | Stewart, Jr. | | |
| 6,540,711 B2 * | 4/2003 | Cox | ..................... | A61F 5/0106 128/116.1 |
| 7,544,161 B1 | 6/2009 | Wooten et al. | | |
| 8,586,091 B2 | 11/2013 | Rimkus et al. | | |
| 2002/0111640 A1 | 8/2002 | Krause et al. | | |
| 2002/0153014 A1 * | 10/2002 | Cheng | ................... | A61F 2/0054 128/885 |
| 2002/0185138 A1 | 12/2002 | Single et al. | | |
| 2004/0112392 A1 | 6/2004 | Parkes | | |
| 2004/0129277 A1 | 7/2004 | Parkes | | |
| 2004/0173219 A1 | 9/2004 | Bakane | | |
| 2008/0011310 A1 | 1/2008 | Anderson et al. | | |
| 2008/0121241 A1 | 5/2008 | Dennis | | |
| 2008/0139949 A1 * | 6/2008 | Caldarone | .......... | A61B 5/02225 600/490 |

OTHER PUBLICATIONS

Declaration of John Allen Pacey, inventor of the present application, with photographs and descriptions of male incontinence control devices.

Extended European Search Report and supplementary European Search report and the European search opinion, EPO Application No. 17894408.8-1122/ 3547877, dated Jan. 20, 2020.

* cited by examiner

DISTRIBUTED PRESSURE FENESTRATED URETHRAL COMPRESSION APPARATUS FOR TREATMENT OF MALE URINARY SPHINCTER DEFICIENCY WITH PRESERVATION OF BLOOD FLOW

TECHNICAL FIELD

The present invention relates to medical devices and more particularly devices used to treat urinary incontinence in males. More specifically the present invention relates to a urethral compression apparatus that uses a fenestrated dorsal hood that applies distributed pressure to the dorsum of the penis and a ventral urethral compressor so that incontinence is resolved and blood flow is maintained.

BACKGROUND

Urinary incontinence in male patients has been an increasingly common problem over the past years in part because of a general trend toward increased longevity, and also due to an increase in urinary tract surgery. Thus, with an increasingly aging population and an increasing number of surgical interventions to treat prostate cancer, the number of males experiencing urinary incontinence has markedly increased. There are a variety of approaches to control of the urine stream from incontinence in males, including management surgically at the bladder neck level, through the use of intra-urethral devices or valves, and by apparatus worn externally and which apply pressure to the penis to compress the urethra.

As examples of surgical management, an implantable controlled valve device known as the AMS 800 is commonly regarded as the surgical standard solution. The AMS 800 is a relatively complex surgical solution; it provides a device that encircles the bulbar urethra with a water-filled ring that is fluidly connected to a valve and a reservoir. The device has been moderately successful in controlling incontinence but while it is very expensive it fails to control urine flow around 30% of the time. Moreover, surgical management always carries risk of complications such as infection and is not indicated for all patients.

Male sling procedures are available examples of other surgical control techniques but like all surgical procedures have some negative outcomes that limit use to very experienced surgical centers.

Another surgical management approach is with magnetic and non-magnetic valves surgically placed at the bladder neck, but these devices have not achieved popularity in clinical practice. Among other reasons for the relatively low levels of acceptance for these devices is the risk of infection that may accompany any device that is positioned in the urethra at the bladder outlet as the foreign body eventually attracts bacterial growth, which cannot be completely eliminated without removal of the nidus of infection.

Intra urethral blocking devices are currently under development and may soon be marketed to compete with the many penile clamps that are known in the marketplace. Examples of current standard penile clamps include the "Dribble Stop" device, the "Cunningham Clamp," a device called the "Squeezer Klip" and others. Yet these centuries old technologies are little better than a clothes peg because of the use of directly opposed compressive parts.

Most early external clamps compromise blood circulation. As an example, the Baumrucker innovation, which is described in U.S. Pat. No. 3,866,611, uses two bars on one side of the clamp and 1 bar on the opposing side. When applied, the opposed clamps guide the penis in a pronounced curve to address incontinence but the device applies pressure to the blood supply in proportion to the pressure on the urethra. The patent describes applying maximal pressure to the dorsal vascular bundle because the single bar of the clamp crosses the top of the penis.

Convenience of use and concern about pressure symptoms are notable factors in acceptance of any externally worn device. Application of sufficient external pressure to the penile shaft to control the increased pressure of a filling bladder has usually resulted in impaired blood flow to or from the penis. The Cunningham Clamp mentioned above is preferred by users in some studies but it has been shown to markedly reduce penile blood flow. It is thus recommended that it be removed every few hours during the day and not used at night because off the risk to the viability of the penile shaft. Generally speaking, there is a dearth of successful devices that have a balance of pressure and leakage that produces a comfortable solution, but in which some amount of urine leakage must be expected. But clamps typically are not used at night because of the pressure symptoms and the concern that continuous 24 hour pressure will cause irritation to the penis, skin, and in the worst possible case ischemic necrosis of the organ. Excessive pressure could result in serious tissue damage when applied at night to users who are non-compos mentis or who have drug-induced sleep.

There are many examples of patented apparatus for treatment of male urinary incontinence. The device described in U.S. Pat. No. 5,842,968 attempted to solve the problem of leakage by using a soft circumferential clamp device that compresses all of the structures of the penis with the same pressure. The device utilizes an inflatable mechanism to produce even distribution of pressure. But the device is inconvenient because it is necessary to carry and use a syringe to relieve or add pressure and there is no attempt to relieve or offset the forces applied on the part of the device that covers the dorsal portion of the penis.

In U.S. Pat. No. 6,349,727, inventor Edward Stewart describes a two-armed device with elastic memory that had a special arm extension that brought pressure to bear on the urethral area. The devise is essentially a transverse clamp with opposing pressure elements that would be expected to impair blood flow through vessels whenever it applies pressure to constrain urethral flow.

U.S. Pat. No. 6,289,895 describes an attempt to provide specific urethral pressure by using a piston that was advanced into a constricted circular penile clamp that provided counter-pressure from the top, in a manner this is not dissimilar to most clamping devices. There is no attempt to diminish the compression of the dorsal arteries with this devise and this results in vascular compression, as with the other known prior art devices. Inventor Shah in U.S. Pat. No. 6,805,662 describes a cylindrical compression device with multiple linear chambers to accommodate greater or lesser amounts of fluid. This device fails to provide pressure selectively to the urethra and there is no circulatory protection.

Finally, the device known as the Jackson Medical J Clamp has been developed in the field and is featured by a large hood and a narrow rubber urethral occluder that has a prominent lever that extends outwardly from the device. Users report that the occluder is position-sensitive, with some positions resulting in leakage. Plus, according to some users the device is difficult to position and requires the user to take care that it does not slip from its position just above the glans penis. The device, which has increased surface area, is not recommended for continuous use.

In view of the foregoing it is clear that there is an ongoing need for a device that is better suited to control incontinence while eliminating the constrained blood flow that is characteristic of the prior art external devices and which makes such prior art devices potentially hazardous to wear at night, and painful due to pressure symptoms.

SUMMARY OF THE INVENTION

The present invention is a urinary incontinence control apparatus that addresses the shortcomings of known devices. The invention as described herein and shown in the drawings defines an effective apparatus for controlling incontinence while allowing a patient to wear the apparatus continually without discomfort and without impairment of circulation. The apparatus may be worn by the patient throughout the range of normal activity for the patient, including patients who are active in sports and the like.

The device according to the present invention addresses these shortcomings of the prior art and includes at least the following characteristics:

Provides improved control of urine flow so that fewer pads are required for backup;

Provides for preferential pressure to the penile urethra while avoiding excessive pressure to the arterial input or venous outflow of blood, thereby alleviating pain and risk resulting from impaired blood flow;

Provides for stable and consistent positioning to avoid slippage during development of increased pressure as the column of urine from the bladder increases;

Provides a solution that is devoid of symptoms caused by mechanical factors related to the weight of the device and interference of the device during movement; the device may be used during sporting activity such as skiing, cycling, running and swimming and the device may be worn during sexual activity;

Allows for effective control of urine leakage with upright posture and during exercise;

Superior comfort such that the user does not feel the presence of the device in a manner that would discourage use;

Provides a single-use foam or other body-contact insert that allows for size adjustment and increased cleanliness by allowing weekly changes of the compression foam, optionally with adhesive backing;

May be worn during erections and sexual activity because, unlike many devices that are designed to sustain erection by constraining the venous return of blood via the dorsal vein and other venous channels, the inventive device does not constrain arterial blood flow;

Does not cause urethritis or skin irritation during use, caused by mechanical properties;

Provides the user with a means for simple adjustment of the quantity of pressure applied during use and determination of whether the pressure should be increased or decreased during use to achieve desired control of leakage;

Allows for continuous use even 24 hours per day, 7 days per week and 365 days per year if the loss of sphincter control causes significant night time leakage;

In one embodiment allows for monitoring and tracking of the pressure applied to the dorsal and urethral side of the penis and creation of an historical record for patients and managers—the amount of pressure applied to the urethra can be compared to leaking events to optimize pressure levels;

Data obtained from monitoring and tracking of pressure from the inventive device, especially during the treatment recovery period following prostatic resection will produce an individual history and create a body of knowledge that will inform clinicians;

Sensors that may be placed in the urethral compression pad and in the dorsal hood provide periodic measurements that are recorded remotely via transmission to remote computers;

In one embodiment, data from the sensors may be used to inform an increase or decrease in urethral pressure by means of a remotely controlled pressure actuator;

In another embodiment the sensors may be defined by a pulse oximeter for monitoring oxygen saturation and/or temperature sensors.

The so-called Rapoport Protocol, which was developed by Dr. Daniel Rapoport, a specialist urological surgeon, describes a supportive guide that specifies care for patients in the post "radical prostatectomy care" situation. The protocol teaches that after catheter removal and a healing period of approximately three weeks the urethral compression device described herein will provide the patient with control of urine flow until restoration of sphincter function occurs. A fundamental problem for such patients is that 60% of postoperative males have incontinence that lasts for 6-12 months and a residual 5-30% of such patients have ongoing urine leakage that can typically be managed only by pads and diapers. A vascular preservation urethral compression device enables postoperative patients to have control of their bodies but a key factor is eliminating the risk of vascular impairment, which could lead to serious adverse conditions including gangrene and venous thrombosis. The present invention provides a solution that solves these problems and addresses the needs of such patients.

The device according to the present invention solves additional problems. There is significant need for a urinary leakage control device for use in nursing facilities to provide round-the-clock urinary control to avoid bed wetting and excessive use of urinary absorption pads. Pads are known to lead to major skin problems, add costs and are associated with offensive odors. The device according to the present invention defines an alternative solution that is safe for use 24 hours per day, 7 days per week, year around. The device is safe because when used with consistent and appropriate distributed pressure the vascular supply to the penis is not compromised and the patient is thus not at risk of necrosis of the external genitalia. Further, the inventive device may be used with the non-compos mentis patient.

There is a compelling need for a device that meets the foregoing challenges. More specifically, there is a documented need for a device that provides excellent control of urine leakage during the day and night without compromising circulation of blood. Known devices exemplified by those described above rely on hourly or other periodic release of pressure to prevent damaging vascular effects and to relieve pain and discomfort.

In a first preferred and illustrated embodiment the urethral compression apparatus according to the invention is defined by a semi-cylindrical fenestrated dorsal hood that is worn dorsally on the penis and which is interconnected with a strap to a urethral compressor that is oriented ventrally to apply compressive pressure on the urethra to prevent urine leakage. The dorsal hood and the urethral compressor apply distributed pressure that prevents compromised circulation but complete prevention of incontinence. The device may be worn continually and is easily removed to allow voiding, then reattached. The fenestration in the dorsal hood (or plural fenestrations as the case may be) allows distribution of pressure to avoid venous and arterial blood flow interruption. And because the urethral compression apparatus 10 is worn either midway along the penile shaft or toward the base of the shaft, urine does not pool in the urethra.

The dorsal hood is generally C-shaped and, when worn on the dorsal aspect of the penile shaft partially encircles the shaft. The urethral compressor is oriented ventrally and applies the desired pressure to the soft ventral tissues and the urethra. A strap applies tension between the dorsal hood and the urethral compressor, and thus the necessary compression between these two components.

The invention defined herein contemplates use of the urethral compression apparatus in clinical and non-clinical settings and, particularly in the nursing home setting, use of a variety of sensors such as pulse oximetry, temperature and pressure sensors so that clinical staff may monitor the patient's condition. Data from the sensors is transmitted to a remote monitoring station and a cloud based system may be utilized to monitor and inform some nurse-patient interactions such as periodic voiding.

BRIEF DESCRIPTION OF THE DRAWINGS

The invention will be better understood and its numerous objects and advantages will be apparent by reference to the following detailed description of the invention when taken in conjunction with the following drawings.

DETAILED DESCRIPTION OF ILLUSTRATED EMBODIMENTS

Reference is now made to the drawings filed herewith. Because the apparatus according to the present invention is especially designed for use with the human penis, it is appropriate to include a brief discussion of some aspects of the anatomy and physiology of the penis; conventional anatomical terminology is used throughout this description. With specific reference to FIGS. 1 and 21, a representative section of a penis 200 is shown in longitudinal section extending from the glans penis 202 and the external urethral orifice 204 (at the left side of the drawing). The first embodiment of the urethral compression apparatus 10 according to the present invention is illustrated applied to the penis 200 about midway along the shaft 206 of the penis or toward the base of the penile shaft. The urethra 208 extends from the urinary bladder (not shown) along the shaft 206 and terminates at external urethral orifice 204. Similarly, the dorsal vein 210 and a corporal artery 212 extend through the corpus cavernosum 214 along the shaft 206. In the cross sectional views of FIGS. 2 and 22, which are taken midway through the urethral compression apparatus 10 of the invention, the structures shown in FIGS. 1 and 21 may be seen in cross section and of course there are two corporal arteries 212, and the dorsal arteries 216 are also illustrated. The dorsal arteries 216 and the dorsal vein 210 are proximate the dorsal aspect of penis 200, which is identified generally with reference number 218. The ventral aspect of penis 200 is identified generally with reference number 220. The urethra 208 is proximate the ventral aspect of penis 200 and in FIGS. 1, 2, 21 and 22 is shown as being compressed and occluded owing to the application of the urethral compression apparatus 10 according to the invention, as detailed below.

Those of skill in the art will readily understand that the penis 200 is a complex organ and the anatomy is far more complex than illustrated herein; the anatomical detail shown in the drawings is appropriate to the description of the structure and operation of the invention but is not meant to illustrate the full anatomy.

Figure 1:
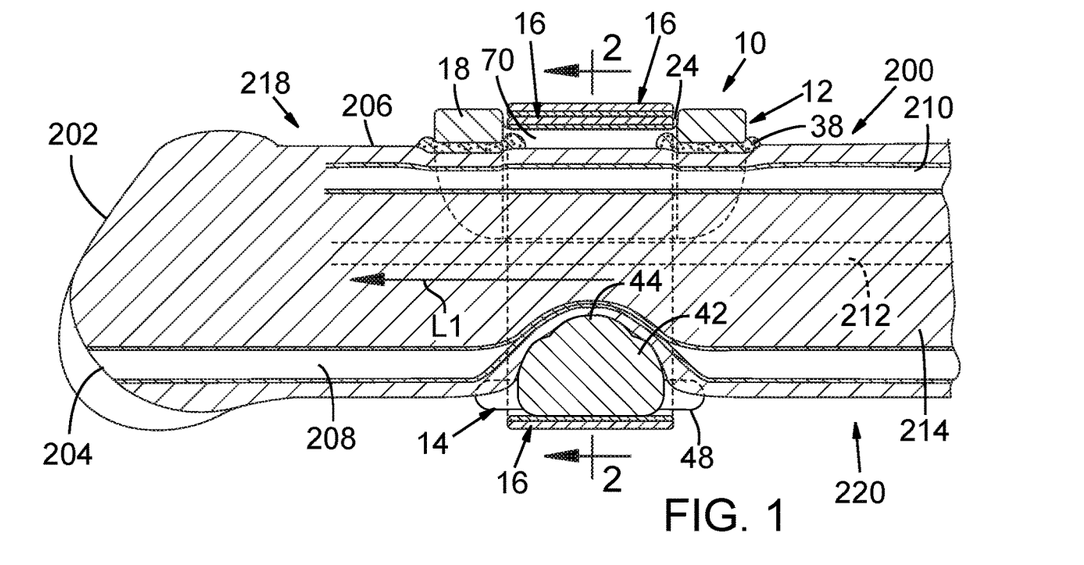
FIG. 1 is a longitudinal sectional and elevational view of a first illustrated embodiment of the present invention applied to a human penis, which also is shown in longitudinal section and which is illustrated with certain anatomical structures to illustrate functional effects of the invention on physiology.
Figure 21:
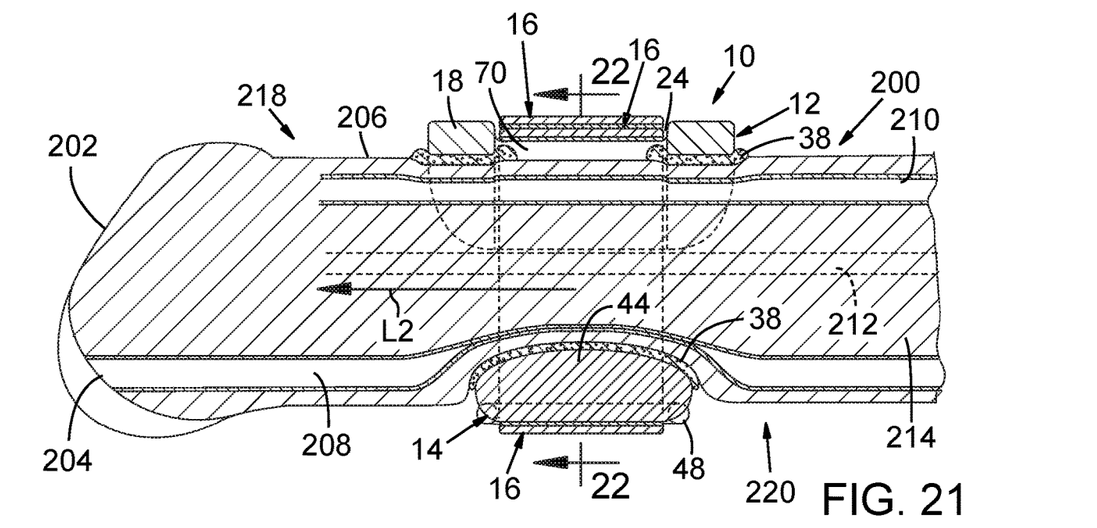
FIG. 21 is a longitudinal sectional and elevational view of a second illustrated embodiment of the present invention applied to a human penis, which also is shown in longitudinal section and which is illustrated with certain anatomical structures to illustrate functional effects of the invention on physiology.

A first illustrated embodiment of the invention will now be described with particular reference to FIG. 1, and FIGS. 3 through 12. Urethral compression apparatus 10 comprises three primary components: a dorsal hood 12; a urethral compressor 14; and a strap 16 that interconnects the dorsal hood 12 and the urethral compressor 14. Each component is described in detail beginning with dorsal hood 12 as shown in FIGS. 7 through 12. Dorsal hood 12 is an arcuate and semi-cylindrical member that in use is designed to extend over and partially encircle the dorsal aspect 218 of penis 200 (FIGS. 1 and 21). In the embodiment of dorsal hood 12 shown in FIGS. 7 through 12, dorsal hood 12 is generally a U or C-shaped body 18 that has a width W (FIG. 10) with first and second arms 20 and 22, and a fenestration 24 between the two arms 20 and 22. The overall shape of dorsal hood 12 may be described as a semi-cylinder in which the two arms 20 and 22 face one another interiorly to define a semi-cylindrical channel or passageway 25 in the dorsal hood. The relative length of the two arms 20 and 22 shown in the figures, and thus the degree to which the dorsal hood 12 encircles the penile shaft, may be varied; it will be appreciated that the dimensions illustrated herein are exemplary but not limiting. For the purposes of illustration only, nominal dimensions of one preferred embodiment of dorsal hood 12 are as follows: height=2.0 cm (dimension H, FIG. 9), and width=3.7 cm (dimension W, FIG. 10). Similarly, a nominal height dimension of urethral compressor 14 may be about 1.5 cm (dimension H, FIG. 4).

Preferably, the dorsal hood 12 is fabricated from a semi-rigid or rigid material because, as detailed below, the dorsal hood 12 is designed specifically to apply distributed pressure to, and avoid excessive pressure on the dorsal aspect 218 of penis 200 and to thereby avoid interference with blood flow, especially through dorsal arteries 216 and dorsal vein 210. In practice the dorsal hood 12 (and other components such as urethral compressor 14) may beneficially be fabricated from a medical grade plastic such as K-RESIN medical grade plastic, although this is but one example. A strap-receiving channel 30 extends over the top of the outer surface 32 of body 18 between edges 34 and 36 and as detailed below, the strap 16 resides generally in the strap-receiving channel 30.

The C-shaped body 18 shown in most of the figures includes a single fenestration 24. It will be appreciated, however, that plural fenestrations may be incorporated into a dorsal hood 12 according to the invention. For example, and by way of illustration with reference to FIG. 8, a second fenestration 26 and a third fenestration 28 may be formed in the opposed first and second arms 20 and 22. Preferably, a soft foam 38 such as an adhesive-backed form is applied over the inner surface 40 of body 18—that is, the surface of body 18 that is oriented toward penis 200 when urethral compression apparatus 10 is in use (FIG. 1) for comfort; the foam 38 does not cover or occlude the fenestration 34 (and if plural fenestrations are used, the foam does not cover or occlude the plural fenestrations). The foam 38 is removed from FIGS. 8 through 11 to better-illustrate the body 18. The specifics and thickness of foam 38 may be varied for customization to accommodate penis size and to, for example, allow the patient to customize the functional characteristics of apparatus 10 as healing progresses and the requirements for incontinence control change. In many post radical prostatectomy patients the degree of pressure applied to the urethra 208 tends to decrease as healing progresses. The urethral compression apparatus 10 described herein allows for simple customization and adjustment to accommodate for a patient's requirements during the healing process.

Turning now to FIGS. 3 through 6 and FIG. 12, a first illustrated embodiment urethral compressor 14 for use with the urethral compression apparatus 10 according to the invention will be described in detail. Urethral compressor 14 comprises a base 42 and transverse ridge 44 that extends upwardly (relative to the respective position of the urethral compressor 14 relative to the dorsal hood 12 when apparatus 10 is in normal use, for instance in FIGS. 1 and 12) and across the base 42. Although there are numerous structures that may be used to interconnect urethral compressor 14 to dorsal hood 12 so that these two components may function together as detailed below, in the embodiment illustrated in FIGS. 3 through 6, urethral compressor 14 includes a pair of strap loops 46 and 48 that are attached to (or formed integrally as part of) base 42 at opposite ends thereof and which define strap through-openings 50 and 52 between the strap loops and the base 42, at opposite ends of the base, and through which strap 16 extends. Urethral compressor 14, like dorsal hood 12, is preferably fabricated in a single, molded part from a medical grade plastic such as K-RESIN medical grade plastic, although again this is but one example.

Figures 7, 8, 9, 10, 12:
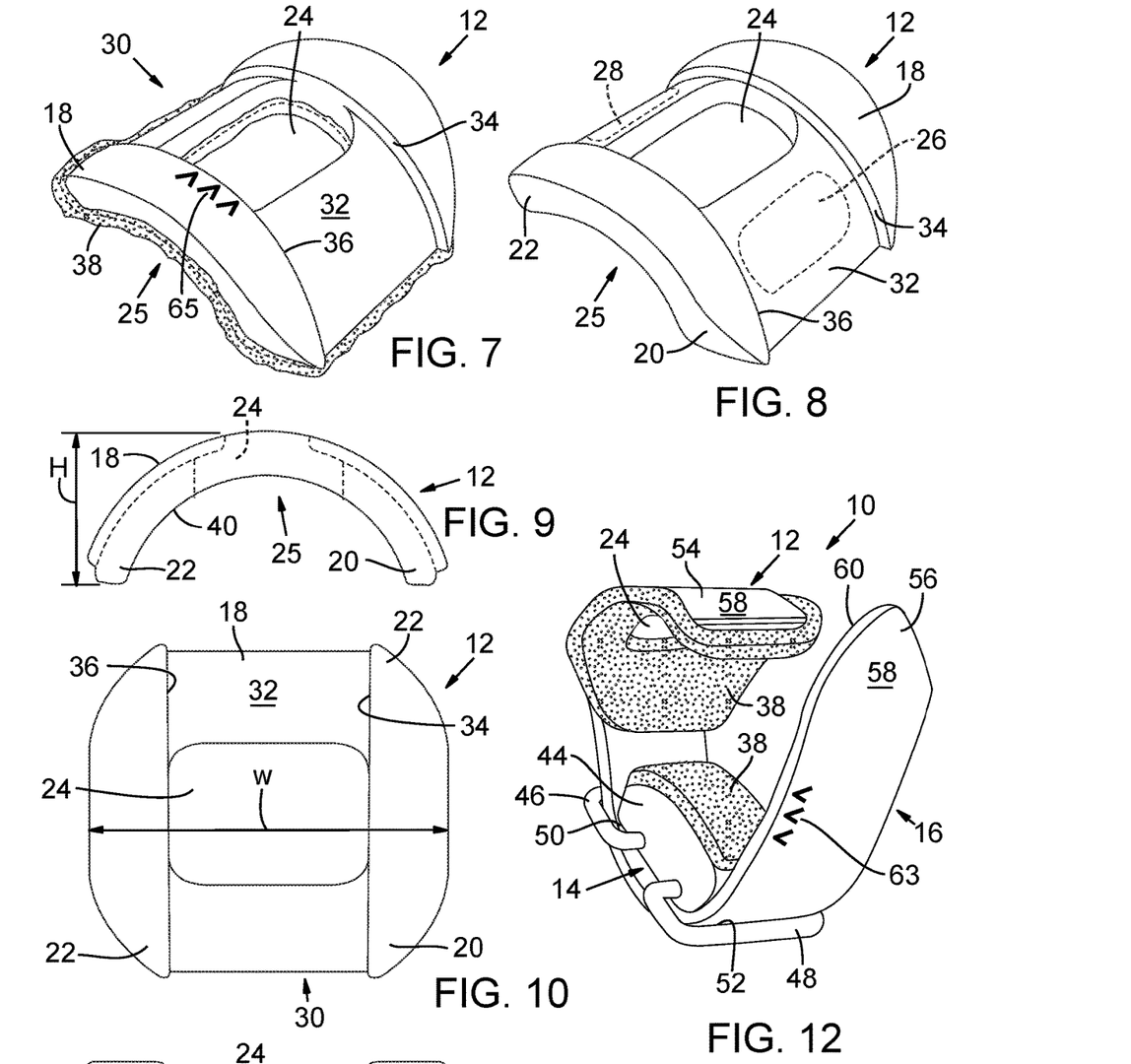
FIG. 7 is a perspective view of the upper or dorsal portion of the embodiment of the invention shown in FIG. 1, in which the dorsal portion, referred to herein as the dorsal hood, is shown in isolation.
FIG. 8 is a perspective view of the dorsal hood shown in FIG. 7 with optional padding removed.
FIG. 9 is an end elevation view of the dorsal hood shown in FIG. 8.
FIG. 10 a top plan view of the dorsal hood shown in FIG. 8.
FIG. 12 is a perspective view of the embodiment of an illustrated embodiment of the present invention, as shown in FIGS. 21 and 22, illustrating the invention with its components assembled with a securing strap shown in a disengaged position. The embodiment illustrated in FIG. 12 is shown with a urethral compressor of the type shown in FIGS. 13 through 17.
Figure 11:
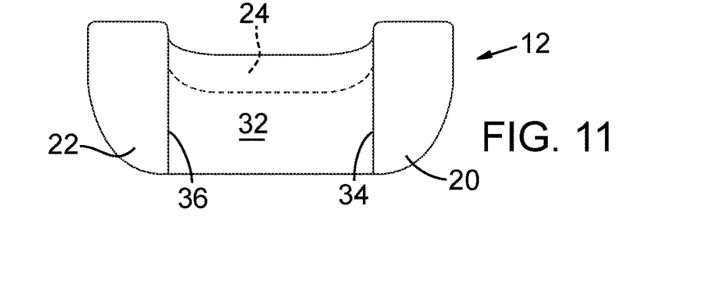
FIG. 11 is a side elevation view of the dorsal hood shown in FIG. 8.

The ridge 44 is referred to as being a "transverse ridge" because when the urethral compression apparatus 10 is in use (see, e.g., FIGS. 1 and 2) the ridge 44 is oriented transverse to the longitudinal axis defined by urethra 208. Thus, in the longitudinal section view of FIG. 1 the section defines a longitudinal axis of the penis 200—that is, line L1. The ridge 44 of the urethral compressor 14 is transverse to this longitudinal axis as shown by line L1 of FIG. 3. Urethral compressor 14 may optionally be fitted with soft foam covering as shown in FIG. 12, and while foam may increase comfort the foam is optional. It will further be appreciated that the shape of the strap loops 46 and 48 may be varied. As one example, in FIG. 12 the strap loops 46 and 48 are more rectangular in shape relative to the shape of the strap loops 46 and 46 of FIG. 3—the particular shape is unimportant so long as the loops allow the strap to interconnect the urethral compressor 14 to the dorsal hood 12.

With reference now to FIG. 12 an assembled urethral compression apparatus 10 is shown. A first end 54 of strap 16 is attached to dorsal hood 12 at outer surface 32 of body 18 between edges 34 and 36 so that the strap 16 resides generally in the strap-receiving channel 30 of the dorsal hood. The strap extends over fenestration 24. The strap runs through opening 50 between strap arm 46 and base 42, beneath base 42, and through opening 52 between strap arm 48 and base 42, so that the second end 56 of strap 16 defines a free end of the strap. Strap 16 is preferably a hook and loop type of fastener material so the second, free end 56 may be looped over the first end 54 and attached thereto. For instance, the outer-facing surface 58 of strap 16 at first end 54 may be hook material and the inner-facing surface 60 of free end 56 may be loop material so that the free end 56 may be looped over the first end and secured thereto. The urethral compressor 14 is slidable relative to strap 16. Said another way, the strap is not fixedly attached to the urethral compressor but instead simply extends through the strap openings 50 and 52. As such, the position of the urethral compressor 14 along the strap may be varied according to a particular user's needs as detailed below.

Figure 13:
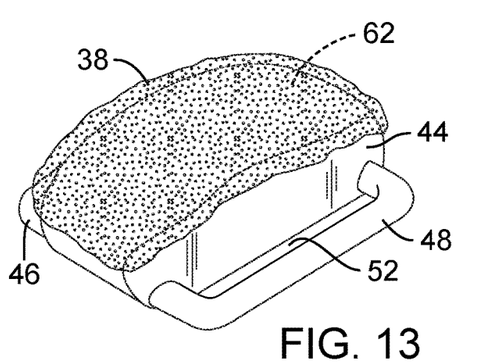
FIG. 13 is a perspective view of a second illustrated embodiment of a urethral compressor as shown in FIG. 12, in which the urethral compressor is shown in isolation and in which padding is shown.
Figure 14:
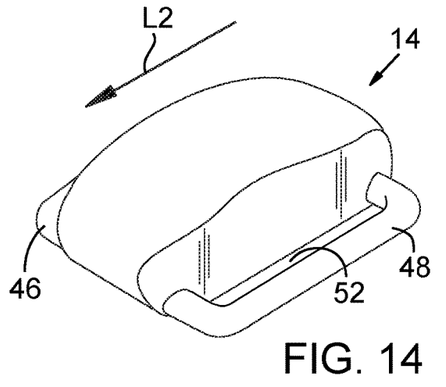
FIG. 14 is a perspective view of the urethral compressor of FIG. 13 in which the padding is removed.

A second illustrated embodiment of a urethral compressor 14 is illustrated in FIGS. 13 through 17 the same reference numbers are used to identify like structures in the urethral compressor 14 shown in FIGS. 3 through 6. Thus, in the embodiment of FIGS. 13 through 19 a base 42, has strap arms 46 and 48 that define openings 50 and 52 between the strap arms and the base 42, through which the strap 16 may extend as detailed above. The optional foam 62 that may be used to cover the base 44 is shown in FIG. 13. The base 42, of the urethral compressor 14 shown in FIGS. 13 through 17 defines a longitudinal axis (line L2 in FIG. 14) that is generally aligned with and parallel to the longitudinal axis of the urethra 208 as described above (i.e., line L1, FIG. 1). The base 42, shown in FIGS. 13 through 17 is interconnected with a dorsal hood 12 with a strap 16 in the same manner as described above.

Figures 15, 16, 17, 18, 19:
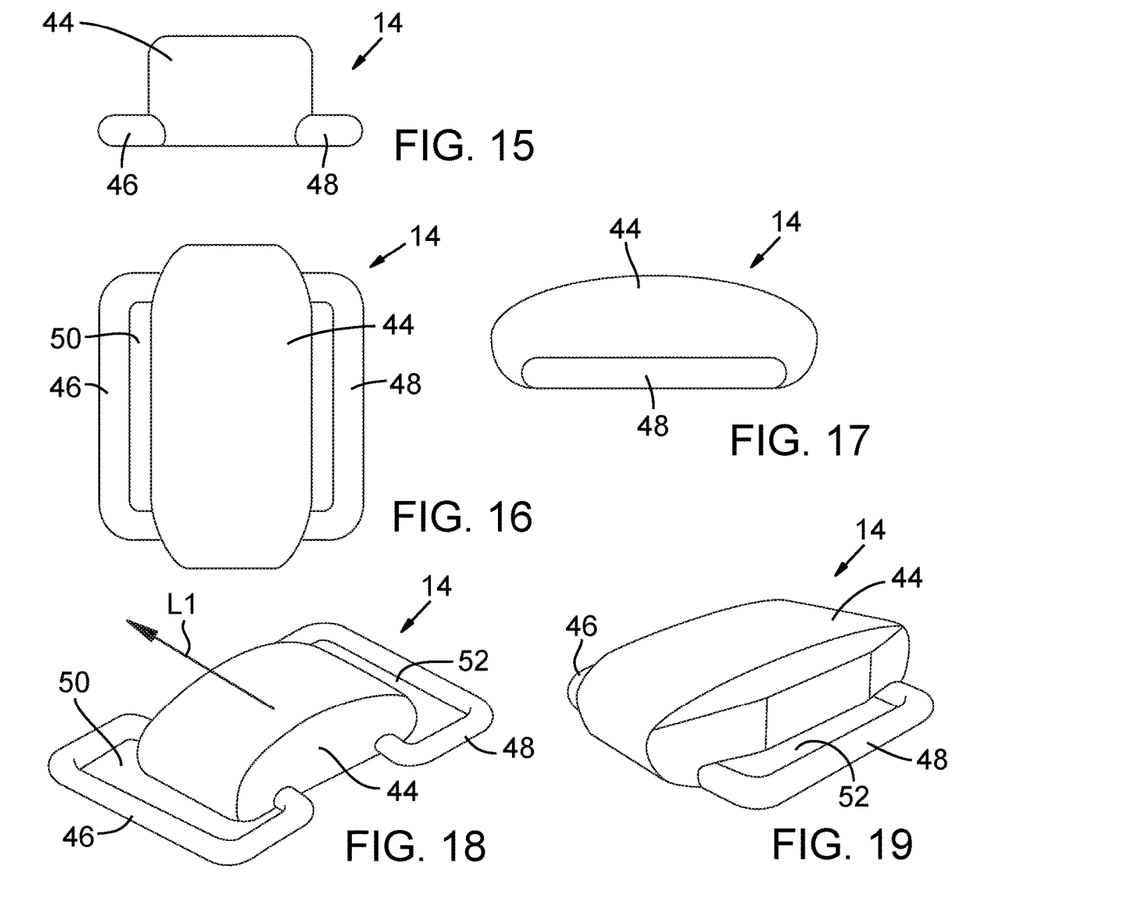
FIG. 15 is an end elevation view of the urethral compressor shown in FIG. 14.
FIG. 16 is a top plan view of the urethral compressor shown in FIG. 14.
FIG. 17 is a side elevation view of the urethral compressor shown in FIG. 14.
FIG. 18 is a perspective view of an alternative design for a urethral compressor according to the invention.
FIG. 19 is a perspective view of yet another alternative design urethral compressor according to the invention.

Two additional embodiments of a urethral compressor 14 according to the invention are illustrated in FIGS. 18 and 19 in which the same reference numbers are assigned to the same structures as those described above. The bases 44 shown in FIGS. 18 and 19 are interconnected with a dorsal hood 12 with a strap 16 as described above.

From the several embodiments of the urethral compressors 14 shown in the figures it will be appreciated that there are several differently shaped structures that provide the equivalent functionally desired attributes described below when paired with the dorsal hood 12 illustrated and described herein.

Figure 23:
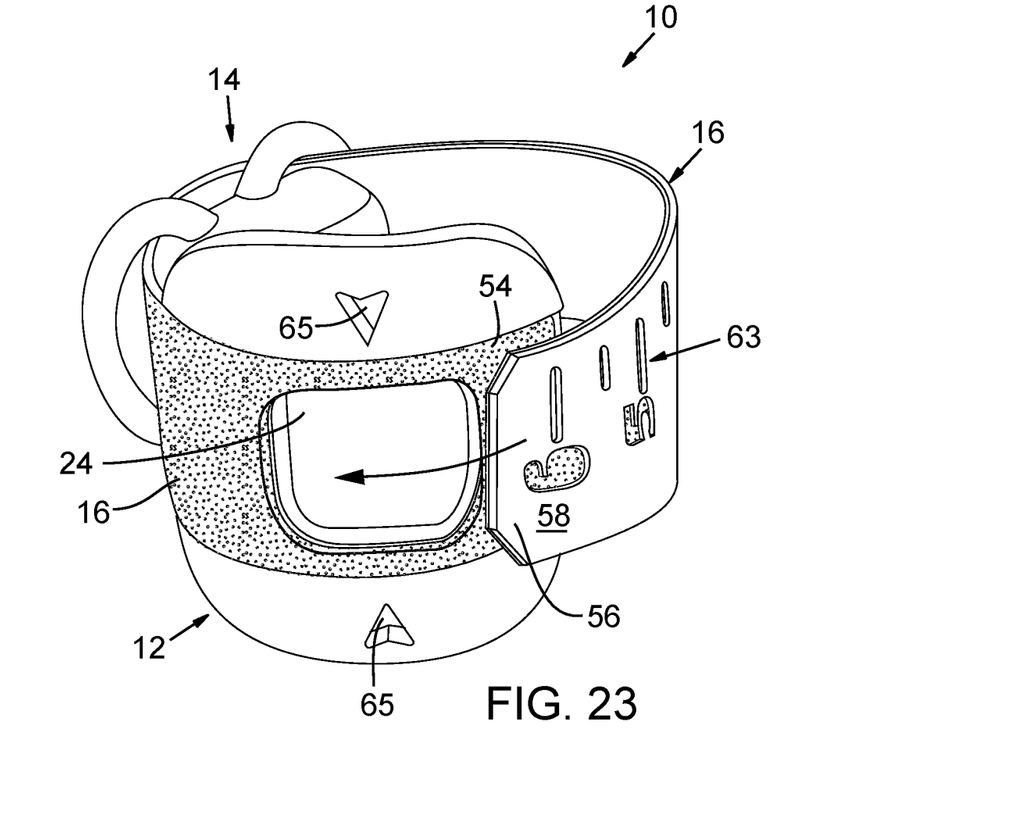
FIG. 23 is a perspective view of yet another alternative embodiment of a urethral compression apparatus according to the invention.

A third illustrated embodiment of a urethral compression apparatus 10 is illustrated in FIG. 23 and again, the same reference numbers are used to identify like structures shown in other figures. In the embodiment of FIG. 23 the strap 16 is itself cut away, i.e., fenestrated, where the strap extends over fenestration 24 in dorsal hood 12 (rather than the strap extending over the fenestration 24 as shown in the embodiment of, for instance, FIG. 12). This leaves the fenestration 24 open until the free end 56 of strap 16 is secured to the first end 54. The adjustment indicia 65 and 65 shown in FIG. 23 are numeric and typically would be even incremental spacing such as 1 cm increments.

Figure 2:
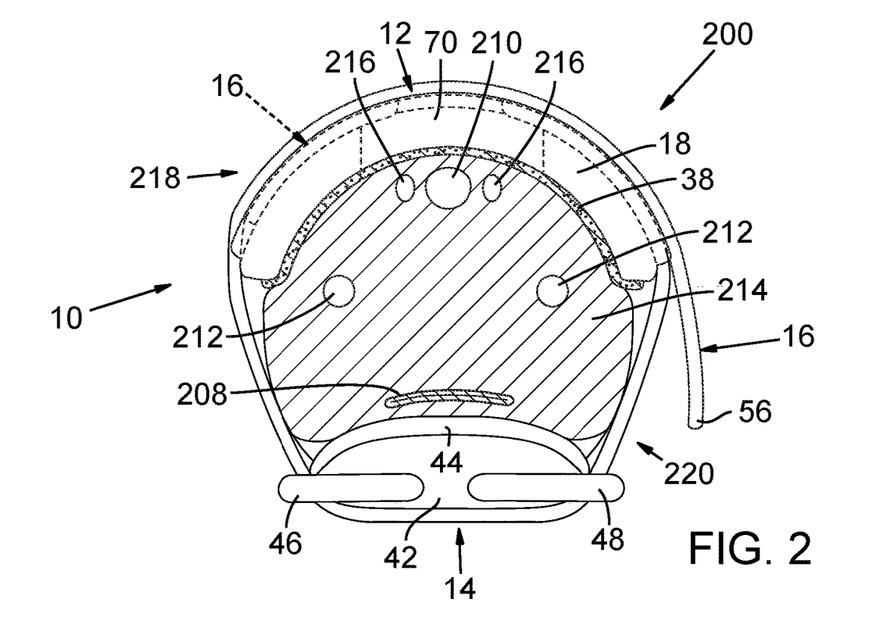
FIG. 2 is a cross sectional view taken along the line 2-2 of FIG. 1. The urethral compression apparatus shown in FIGS. 1 and 2 is shown with a dorsal hood of the type shown in FIGS. 7 through 11, and a urethral compressor of the type shown in FIGS. 3 through 6.
Figure 3:
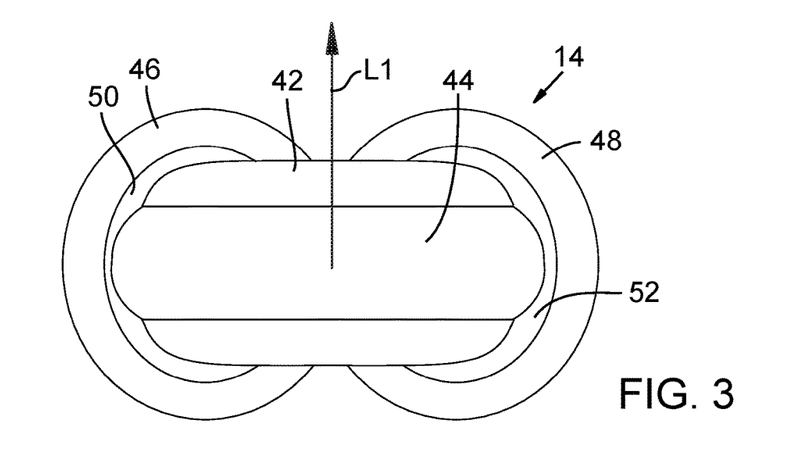
FIG. 3 is a top plan view of an illustrated embodiment the lower or ventral portion of the invention, referred to herein as the urethral compressor.
Figure 4:
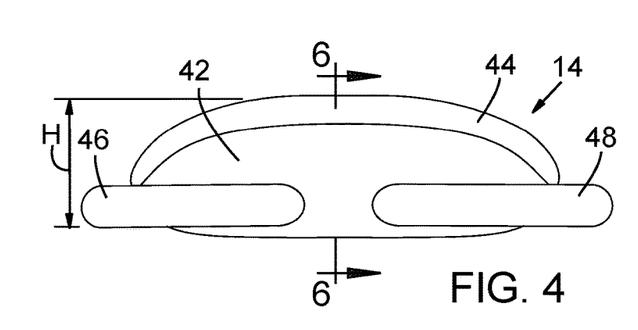
FIG. 4 is a side elevation view of the ventral portion shown in FIG. 3, in which the urethral compressor is shown in isolation.
Figure 5:
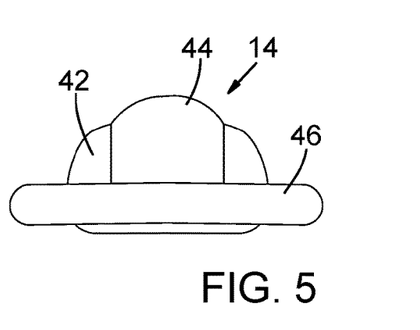
FIG. 5 is an end elevation view of the urethral compressor shown in FIG. 3.
Figure 6:
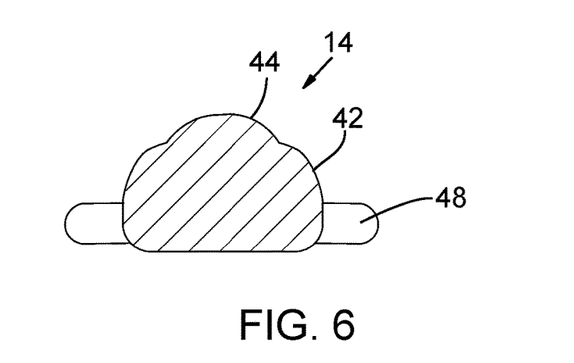
FIG. 6 is a cross sectional view of the v shown in FIG. 3 and taken along the line 6-6 of FIG. 3.

When urethral compression apparatus 10 is applied to penis 200 as shown in FIGS. 1, 2, 21 and 22, the body 18 of dorsal hood 12 is oriented over the dorsal aspect 218 of penis 200 midway along the penile shaft such that the fenestration 24 is oriented over the dorsal aspect such that the shaft of the penis is in channel 25 of the hood. A gap or space 70 is defined between strap 16 and the dorsum of the penis at fenestration 24 so the strap does not contact the penis and does not apply pressure directly to the penis. The inner surface 40 of dorsal hood 12 is in direct contact with the penis 200 (i.e., the foam 38 is in direct contact) but the structure of body 18 with its width W, its first and second arms 20 and 22, and a fenestration 24 between the two arms 20 and 22 applies a relatively evenly distributed pressure over the dorsal aspect of the penis to avoid excessive point pressure where the dorsal arteries and veins reside. The fenestration 24 and the gap 70 allows for some penile tissue to enter the fenestration and the space 70 so that pressure on the dorsal aspect of the penis is distributed and minimized so that circulation is not compromised. The user places the dorsal hood 12 as illustrated and the urethral compressor 14 is oriented ventrally, or inferiorly and caudad relative to the dorsal hood, as shown. As noted, the first end 54 of strap 16 is adhered to dorsal hood 12 (for instance, with suitable adhesives or by stitching and the like) and the position of the urethral compressor 14 on strap 16 may be varied according to a particular patient's needs. More specifically, a patient orients the urethral compressor 14 on strap 16 so that when the apparatus 10 is applied to the patient's penis 200 the urethral compressor 14 is oriented ventrally on the penis and preferably bilaterally centered, as shown in FIG. 2. With urethral compression apparatus 10 oriented in this position the free end 60 of strap 16 is looped over the first end 54 and attached thereto with the facing hook and loop materials. The patient is able to fasten the strap 16 so that the transverse ridge 44 of base 42, applies the proper amount of pressure to compress the urethra 208, as shown, but does not compromise circulation through the dorsal vein 210 and the corporal artery 212. When the strap 16 is attached in this manner the circular enclosure defined by apparatus 10 is closed caudad to the dorsal hood 12 by the detachable, urethral compressor 14 and apparatus 10 is adjustable to apply variable pressure to the longitudinal urethral surface to transmit pressure through the soft tissue on the ventral aspect of the penis to effectively prevent leakage of urine. Indexing markings or indicia 63 on the second end of strap 16 (FIGS. 12 and 23) and corresponding indexing indicia 65 on either the dorsal hood 12 (as shown in FIG. 7), may be included so that the patient is able to secure the strap repeatedly in the same position so that the same pressure is applied. The indicia may be either alpha or numeric characters, as also shown in FIG. 23.

The pressure applied by dorsal hood 12 with its fenestration 24 is distributed over a substantial area of the penile shaft, defined by the interior surface area of interior surface 40 of dorsal hood 12. By distributing pressure over an increased surface area, combined with the fenestration(s) significantly decreases the amount of point pressure that is applied to the dorsal aspect of penis 200 so that circulation in the nearby arteries and veins is not compromised, yet allowing sufficient pressure to be applied to the ventral aspect of the penis 200 to occlude the urethra 208. This orientation is shown in FIG. 2. As a result, the apparatus 10 applies lower average pressure to the penis over a greater surface contact area so that there is no adverse pain or tissue effects, and no impairment of circulation even over extended periods of use. In addition the C-shape of the dorsal hood 12, combined with the urethral compressor 14 and strap 16 results in a device that is not prone to slipping once it is properly fitted.

Testing has confirmed that the transverse ridge 46 of the urethral compressor 14 shown in FIGS. 1 and 2 is highly effective in preventing urine leakage with the apparatus 10 fitted very comfortably so that arterial and venous circulation is not compromised. As illustrated, the transverse ridge 46 (L2, FIG. 3) extends generally at right angles to the longitudinal axis L1 of the urethra 208. As a result, the patient is able to wear apparatus 10 continually and to participate in all aspects of normal daily activity including sports, etc. without incidence of incontinence. And as noted, the C-shaped body 18 of dorsal hood 12 has proven to insure proper placement and orientation of the urethral compression apparatus 10 without slipping for long periods of time. This is due to the C-shaped dorsal hood 12, which fixes the position of apparatus 10 on penis 200 in the sagittal plane with the semi-cylindrical enclosure defined by the opposed arms 20 and 22 essentially at least partially surrounding and cradling the penile shaft. Doppler testing has confirmed that pulsatile blood flow is not compromised when the apparatus 10 is worn as detailed above.

Testing has also confirmed that the rigidity or semi rigidity of the dorsal hood 12 prevents circumferential compression of the penis during use of apparatus 10 so that normal physiological enlargement and shrinking of the penis does not interfere with the primary function of the apparatus 10, namely, prevention of urine leakage. Periodic removal of apparatus 10 to allow urine voiding is a very simple procedure, as is reinstallation of apparatus 10 subsequent to voiding.

Figure 22:
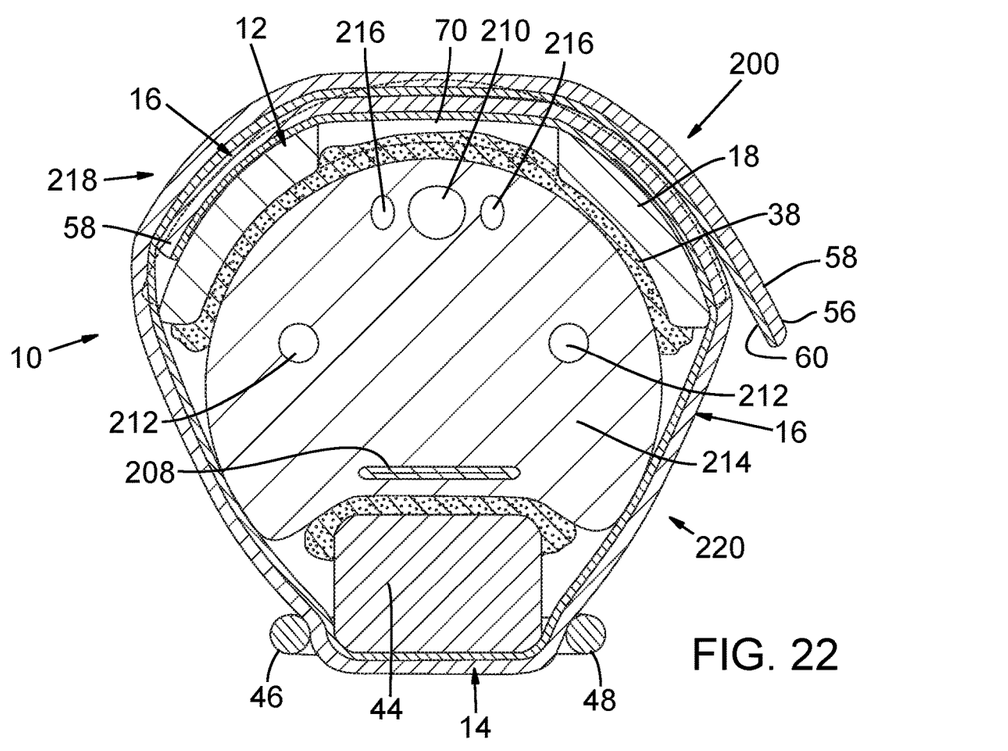
FIG. 22 is a cross sectional view taken along the line 22-22 of FIG. 21. The urethral compression apparatus shown in FIGS. 21 and 22 is shown with a dorsal hood of the type shown in FIGS. 7 through 11, and a urethral compressor of the type shown in FIGS. 13 through 17.

FIGS. 21 and 22 illustrate an urethral compression apparatus 10 according to the invention in which a urethral compressor 14 of the type shown in FIGS. 13 through 17 is utilized. Functionally, the apparatus 10 in FIGS. 21 and 22 performs identically to the embodiment of apparatus 10 described above in respect of FIGS. 1 and 2. However, the urethral compressor 14 applies pressure to the ventral aspect of the penis in a substantially parallel orientation to the axis of the urethra 208. In other words, the longitudinal axis of the base 42 (i.e., line L2, FIG. 14) is oriented parallel to the longitudinal axis L1 of penis 200 and thus urethra 208. In this instance the urethral compressor 14 applies a linearly distributed pressure on the ventral aspect of the penile shaft to compress the urethral lumen over relatively more extended length compared to the embodiment of FIG. 1.

All of the embodiments of the urethral compressor illustrated in FIGS. 3, 14, 18 and 19, when used with the dorsal hood 12 as described, provide sufficient pressure to the ventral aspect of the penis to compress the urethra 208 to eliminate incontinence and all the while providing a highly comfortable fit. In practice, a patient may choose the urethral compressor 14 that is the most comfortable and effective for that particular patient—regardless of which design is used, the apparatus 10 may be worn continuously without pain and without risk of compromised circulation.

It will be appreciated that the strap 16 defines a readily and easily adjustable means of attaching and securing the dorsal hood 12 to the urethral compressor 14 and that there are numerous equivalent ways of attaching the two parts together other than the described hook and loop fabric. Thus, other types of tensioning bands such as a band with holes in one end with anchoring pins on the overlapping portion may be used. In addition, the dimensions of the dorsal hood 12 may be varied so that a size appropriate to individual patient may be selected.

Figure 20:
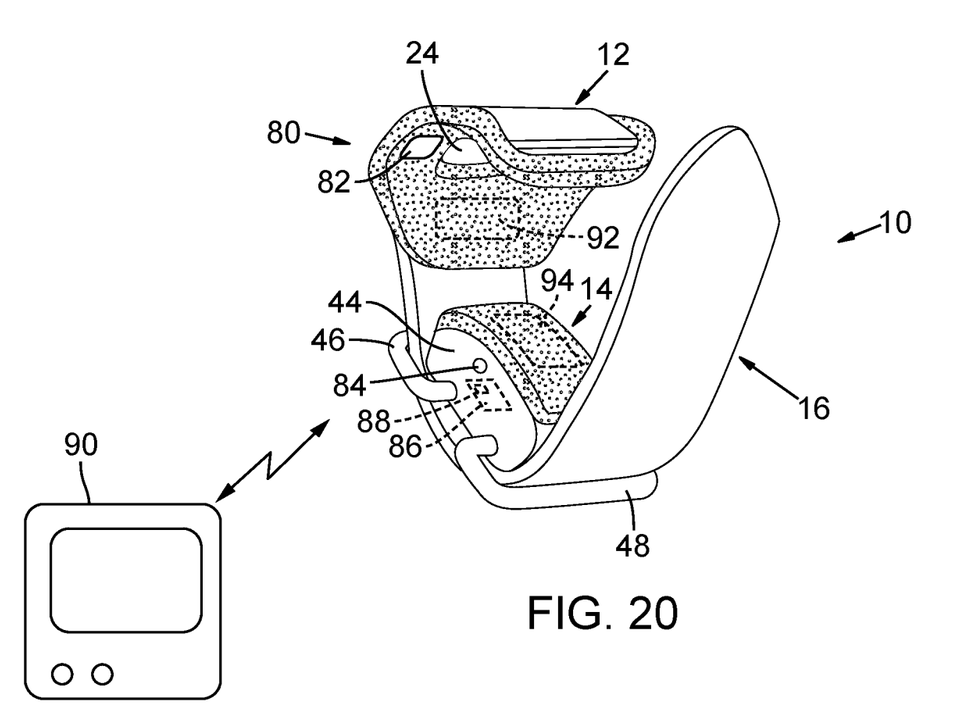
FIG. 20 is a schematic illustration of a urethral compression apparatus according to the present invention in which sensors defining a pulse oximeter are incorporated, and including remote monitoring capabilities.

Reference is now made to FIG. 20, which illustrates somewhat schematically some of the various sensors that may be used with urethral compression apparatus 10 to enable effective remote monitoring of the apparatus by clinical staff. In the first instance, urethral compression apparatus 10 may include a transmissive pulse oximeter, shown generally with reference number 80 and including a light transmitter 82 in the interior-facing portion of dorsal hood 12 and a correspondingly placed photodetector 84 in urethral compressor 14. A power supply and (as detailed below) electronic package 86 may be installed interiorly in base 42 of urethral compressor 14, or for example on the bottom side of the base. Pulse oximeter 80 conventionally passes two wavelengths of light from light transmitter 82 through the patient's penis 200 to the photodetector 84. The changing absorbance of light due to pulsing arterial blood is analyzed in known manners with the control module 86 to generate oxygen saturation data and to measure and monitor the patient's oxygen saturation to insure that circulation is not compromised. A reflective pulse oximeter may be used as well.

Control module 86 includes a power supply 88 and circuitry and associated software and/or firmware to facilitate operation of the pulse oximeter 80 and preferably is wirelessly enabled (with standard wireless communication protocols such as Bluetooth) so that data from the pulse oximeter may be transmitted to a remote monitoring station 90. This allows clinical staff to remotely monitor patients wearing the urethral compression apparatus 10 to insure adequate circulation.

Other types of sensors may be incorporated into urethral compression apparatus 10, including for example temperature and pressure sensors. As an example, a temperature sensor 92 may be incorporated in dorsal hood 12 (or in urethral compressor 14) and/or a pressure sensor such as a foil-type strain gage 94 or other equivalent pressure sensor may be incorporated in urethral compressor 14 (and/or in dorsal hood 12). Each of these types of sensors is attached with appropriate circuitry to control module 86 so that temperature and/or pressure data may be transmitted to remote monitoring station 90 for evaluation by clinical staff. Software in remote monitoring station 90 includes threshold alarms to alert staff to out-of-bounds conditions such as low oxygen saturation values, increased temperature or pressure values. A urethral compression apparatus 10 may further include conventional electronics connections to allow the apparatus to be connected by hard wiring to the monitoring station 90 in clinical settings where wireless connections cannot be utilized.

In addition to data from the various sensors may being transmitted to the remote monitoring station 90, data may be transmitted to and stored in a cloud computing environment for access by care providers. The system may be set up to provide routine and periodic notifications to the healthcare professionals, for example, making sure that the patient voids urine regularly.

The strap 16 defines a means for adjusting the pressure applied to the penis by urethral compression apparatus 10 but the strap described above and shown in the drawings may be replaced with other equivalent devices for accomplishing the same function. As just one example, an automated (and if desired, remotely controlled) pressure actuator such as a pneumatic or electrically drive actuator may be used as a pressure application means.

While the present invention has been described in terms of preferred and illustrated embodiments, it will be appreciated by those of ordinary skill that the spirit and scope of the invention is not limited to those embodiments, but extend to the various modifications and equivalents as defined in the appended claims.

The invention claimed is:

1. Urinary incontinence control apparatus, comprising:
a semi-cylindrical dorsal hood adapted for positioning on a dorsal aspect of a penis and defining a semi-cylindrical channel and having an exterior surface, an interior surface facing the semi-cylindrical channel, and at least one bounded fenestration defining an opening extending through the dorsal hood from the exterior surface through the interior surface between first and second ends of the dorsal hood, the at least one bounded fenestration positioned above dorsal arteries and dorsal veins of the penis when the dorsal hood is positioned on the dorsal aspect;

a urethral compressor positioned on a ventral aspect of the penis below the at least one bounded fenestration when the dorsal hood is positioned on the dorsal aspect;

a strap interconnecting the dorsal hood and the urethral compressor such that the dorsal hood, urethral compressor, and the strap is configured to encircle the penis and such that the urethral compressor is retained 180 degrees from the at least one bounded fenestration to thereby decrease pressure applied to the dorsal arteries and dorsal veins of the penis, wherein the strap extends from the first end of the dorsal hood, over the at least one bounded fenestration, past the second end, under the urethral compressor and over the first end.

2. The urinary incontinence control apparatus according to claim 1 in which the urethral compressor includes a ridge facing the semi-cylindrical channel and extending transverse to a longitudinal axis of the dorsal hood.

3. The urinary incontinence control apparatus according to claim 2 in which the urethral compressor includes a main body and a first loop at a first end of the main body and a second loop at a second end of the main body, wherein each loop defines a space between the respective loop and the main body.

4. The urinary incontinence control apparatus according to claim 3 in which the strap extends from the dorsal hood through the space between the first loop and the main body, beneath the urethral compressor, through the space between the second loop and the main body, and over the dorsal hood.

5. The urinary incontinence control apparatus according to claim 4 in which the dorsal hood further defines a strap channel on the exterior surface and the strap extends over the strap channel.

6. The urinary incontinence control apparatus according to claim 5 wherein a first end of the strap is connected to the dorsal hood and a second end of the strap is a free end, and wherein the second end of the strap is connectable to the dorsal hood.

7. The urinary incontinence control apparatus according to claim 6 wherein the strap extends through the strap channel and over the at least one fenestration such that there is a space in the at least one fenestration between the interior surface and the strap.

8. The urinary incontinence control apparatus according to claim 1 including a pulse oximeter adapted for measuring oxygen saturation.

9. The urinary incontinence control apparatus according to claim 8 in which the pulse oximeter generates oxygen saturation data, and the apparatus further including means for transmitting the oxygen saturation data to a remote monitoring station.

10. The urinary incontinence control apparatus according to claim 1 including a pressure sensor adapted for transmission of pressure data to a remote monitoring station.

11. The urinary incontinence control apparatus according to claim 1 including a temperature sensor adapted for transmission of temperature data to a remote monitoring station.

12. Urinary incontinence control apparatus, comprising:
a substantially C-shaped dorsal hood having an interior surface adapted for positioning on a dorsal aspect of a penis and at least partially surrounding the penile shaft, and an exterior surface, the dorsal hood having at least one bounded opening extending through the dorsal hood, the at least one bounded opening located on the C-shaped dorsal hood between first and second ends of the C-shaped dorsal hood so that the at least one bounded opening is configured to be positioned on the dorsal aspect of the penile shaft above dorsal arteries and dorsal veins;

a urethral compressor caudad to the dorsal hood and the at least one bounded opening and having a urethral compressing component facing the interior surface of the dorsal hood below the at least one bounded opening such that the urethral compressing component is configured to apply pressure to a ventral aspect of the penile shaft to thereby occlude the urethra, wherein the at least one bounded opening is configured to be positioned on the dorsal aspect of the penile shaft to minimize pressure on the dorsal aspect of the penile shaft and the dorsal arteries and dorsal veins; and a connector interconnecting the dorsal hood with the urethral compressor so that the urethral compressor is configured to be retained on the ventral aspect of the penile shaft and for varying the pressure applied to thereto, the connector extending from the first end of the C-shaped dorsal hood, over the at least one bounded opening, past the second end, beneath the urethral compressor and over the first end.

13. The urinary incontinence control apparatus according to claim 12 in which the connector is defined by a strap having a first end attached to the C-shaped dorsal hood and a second free end and wherein the urethral compressor is movable relative to the strap.

14. The urinary incontinence control apparatus according to claim 12 further comprising an oximeter for generating penis blood oxygen saturation data.

15. The urinary incontinence control apparatus according to claim 13 further including means for transmitting the penis blood oxygen saturation data to a monitoring station.

16. Urinary incontinence control apparatus, comprising:
a semi-cylindrical component adapted for at least partially encircling a penile shaft in a semi-cylindrical channel extending therethrough and having at least one bounded fenestration configured to correspond to a dorsal aspect of the penis, the at least one bounded fenestration extending through the semi-cylindrical component between first and second ends of the semi-cylindrical component;

a urethra compressor having a urethral compression component facing the semi-cylindrical channel inferiorly to the at least one bounded fenestration; and strap means for connecting the semi-cylindrical component to the urethra compressor, wherein the semi-cylindrical component, urethra compressor and strap means combine to encircle the penile shaft with the strap means extending from the first end of the semi-cylindrical component, over the at least one bounded fenestration, past the second end, under the urethra compressor and over the first end;

wherein the at least one bounded fenestration is configured to be positioned on the dorsal aspect of the penis 180 degrees from the urethra compressor to minimize pressure thereon from the semi-cylindrical component.

17. The urinary incontinence control apparatus according to claim 16 in which the urethral compression component is defined by a ridge extending transverse to a longitudinal axis of the semi-cylindrical channel.

18. The urinary incontinence control apparatus according to claim 17 including an oximeter.

* * * * *